United States Patent [19]

Sagstetter

[11] Patent Number: 4,938,745
[45] Date of Patent: Jul. 3, 1990

[54] NEEDLE GUARD WITH VISUAL CONFIRMATION OF LOCK

[76] Inventor: William E. Sagstetter, 2696 S. Colorado Blvd., Ste. 585, Denver, Colo. 80222

[21] Appl. No.: 234,336

[22] Filed: Aug. 19, 1988

Related U.S. Application Data

[63] Continuation-in-part of Ser. No. 160,150, Feb. 25, 1988, Pat. No. 4,878,902.

[51] Int. Cl.⁵ ................................................ A61M 5/32
[52] U.S. Cl. ..................................... 604/263; 604/198; 128/917
[58] Field of Search ................ 604/110, 111, 192, 198, 604/263; 128/763–765

[56] References Cited

U.S. PATENT DOCUMENTS

4,693,708  9/1987  Wanderer et al. .............. 604/263 X
4,702,738 10/1987  Spencer .......................... 604/263 X
4,731,059  3/1988  Wanderer et al. .............. 604/198 X
4,782,841 11/1988  Lopez ............................. 604/263 X
4,795,432  1/1989  Karczmer ....................... 604/263 X
4,813,940  3/1989  Parry .................................. 604/198

Primary Examiner—C. Fred Rosenbaum
Assistant Examiner—Corrine Maglione
Attorney, Agent, or Firm—Cahill, Sutton & Thomas

[57] ABSTRACT

A non-rotatable axially translatable anterior guard includes a detachable tab for creating an aperture to exteriorize and expose, upon posterior translation along a single or double ended needle supporting hub, the anterior end of the needle ready for use. Upon anterior translation of the anterior guard, it lockingly engages the hub to retain the needle therein. An aperture extends through the hub, which aperture is uncovered only upon locking engagement of the guard, to provide a visually perceivable unambiguous indication that the guard is locked to envelope the anterior end of the needle after use.

46 Claims, 3 Drawing Sheets

NEEDLE GUARD WITH VISUAL CONFIRMATION OF LOCK

REFERENCE TO RELATED APPLICATIONS

This application is a continuation in part application of an application entitled "NEEDLE GUARD FOR BODY SUBSTANCE ISOLATION", Ser. No. 160,150, filed Feb. 25, 1988, and now U.S. Pat. No. 4,878,902 and describing an invention of which the present inventor is a co-inventor.

BACKGROUND OF THE INVENTION

1. Field of the Invention

The present invention relates to a guard device for needles used in medical practice and, more particularly, to visually confirmable positionally lockable guard devices for single and double ended needles.

2. Description of the Prior Art

A needle shield which must be removed anteriorly from a needle hub before a syringe can be used for a medical procedure is well known. Remounting such a shield requires a user to insert the point of the needle into the open end of the shield and draw the shield posteriorly over the needle until it encloses the needle. Such a removable needle shield contains several limitations, including: (1) after a liquid medicament has been drawn up in a syringe, medical personnel may occasionally delay the administration of the medicament, which delay requires retrieval and replacement of the needle shield to prevent contamination of the sterile needle and creates extra steps for busy medical personnel; (2) medical personnel often remove this needle shield by holding the needle shield between their teeth or lips. This practice has been associated with accidental self-puncture in the face or other body parts; (3) in order to recover a used needle with a previously removed needle shield, it is necessary to replace the needle shield back over the pointed end of the used needle, which replacement increases the risk to medical personnel of accidentally puncturing themselves with the pointed end of the used needle; and, (4) if the needle has been accidentally bent during a medical procedure or if the needle shield is replaced over the needle at an incorrect angle, the needle point may inadvertently pierce the side of the needle shield and puncture the fingers or hand.

In order to avoid problems attendant needle shields which must be remounted posteriorly from a location anterior of the needle point, various devices have been developed. Several of these devices include shields translatable posteriorly upon the barrel of a hypodermic syringe to expose the needle. To re-enclose the needle within the shield, anterior translation of the shield is effected. Unless the shield is locked at its anterior end of travel, inadvertent uncovering of the needle may occur. This results in a potential for exposure to needle stick or contact with body fluids upon the needle. If a lock is used it must not be unlockable during normal handling of a discarded syringe and an indication of the locked state should be visually apparent without having to test the positional security of the shield. Furthermore, such indication should be evident in an unambiguous manner under low light conditions.

SUMMARY OF THE INVENTION

A hub of a double ended needle used as part of a blood collection system includes a non-rotatably mounted axially translatable guard for receiving and covering the anterior needle prior and subsequent to use. The guard is mounted upon the hub at a first position prior to use, at a second position after posterior translation of the guard to exteriorize the anterior needle, and at a third position for locking engagement with the hub after anterior translation of the guard to re-enclose the anterior needle. The hub is perforated at a location exposed by the guard only upon placement of the guard in the third position to provide an unambiguous visually apparent cue that the guard is in the permanently locked position. In a single needle variant having a posteriorly translatable and lockable guard, a similar cue can be provided upon or within the barrel of the syringe. A removable tab at the anterior end of the guard provides an aperture through which the needle is exteriorized.

It is therefore a primary object of the present invention to provide a positive and unambiguous visually apparent indication that a guard for the anterior needle of a double ended needle is in an anterior locked position.

Another object of the present invention is to provide a non-detachable lockable guard for shielding a single ended needle before and after use.

Yet another object of the present invention is to provide an axially translatable non-rotatable guard for maintaining sterile a single ended needle prior to use and for guarding against contact by a user of the single ended needle after use.

Still another object of the present invention is to provide a visually perceivable indication that a non-detachable guard for a single ended needle is, after use of the needle, in a locked position to shield the needle.

A further object of the present invention is to provide in the hub of a single or double ended needle with an aperture exposed only upon the positioning of a needle guard in its anterior locked position to shield the needle.

A yet further object of the present invention is to provide a light transmissible aperture in the hub of a single or double ended needle which accommodates transmission of light only upon placement of a guard for the anterior needle in its anterior and locked position.

A still further object of the present invention is to provide a method for indicating in an unambiguous manner the placement of a guard in a locked position to enclose a single ended needle.

A still further object of the present invention is to provide a method for locking a needle guard in place after use of a double ended needle and for simultaneously providing a visually perceivable affirmation of the guard being locked in place.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 9 is a cross sectional view taken along lines 9—9, as shown in FIG. 4;

DETAILED DESCRIPTION OF THE PREFERRED EMBODIMENT

Figures 1, 2:
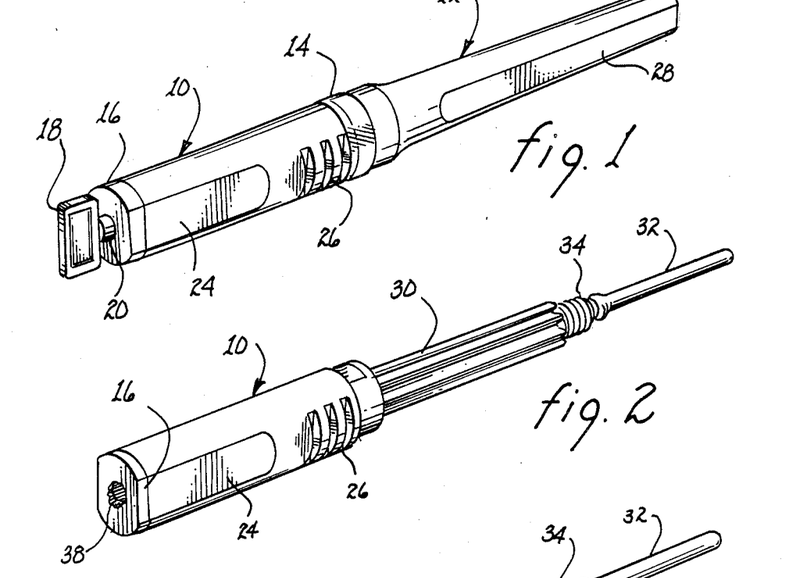
FIG. 1 illustrates a pair of guards for protecting a double ended needle.
FIG. 2 illustrates exposure of the posterior end of the double ended needle.

Referring to FIG. 1, there is shown a double ended needle enclosed within an anterior guard 10 and a posterior guard 12. The junction therebetween is sealed with a band of conventional sealing tape 14. As the two guards and sealing tape are essentially impermeable, the enclosed double ended needle can be maintained sterile for a indeterminate period. The anterior guard includes a cap 16 having a tab 18 formed as part of the cap through frangible boss 20.

Anterior guard 10 and posterior guard 12 are predominately oval or oblong in cross section to minimize rolling upon a surface and to prevent rotation of the guards relative to the longitudinal axis of the enclosed needle. Anterior guard 10 may include opposed flats 24 to assist in gripping the guard along with segmented grooves 26 to assist a user in gripping and manipulating the guard. Similarly, posterior guard 12 may include opposed flats 28 and grooves (not shown).

Figures 3, 6:
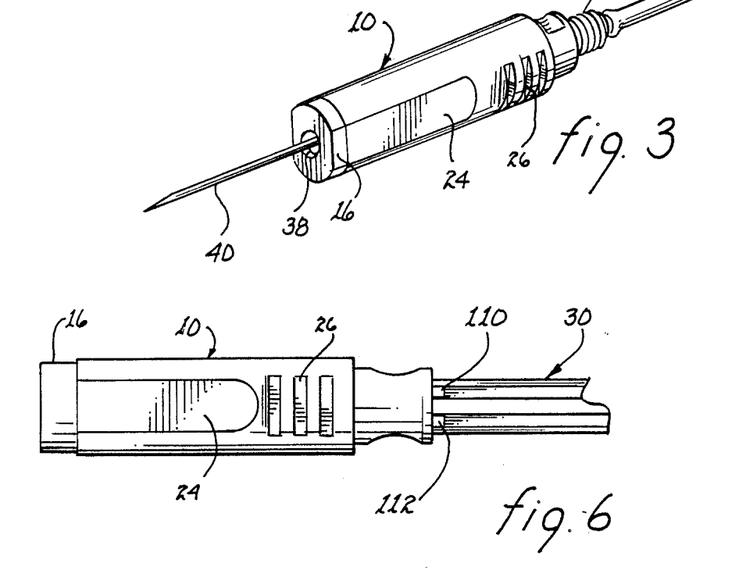
FIG. 3 illustrates posterior translation of the anterior guard attendant the anterior needle of the double ended needle.
FIG. 6 is a partial side view of the anterior guard in the locked position.

To expose the double ended needle for use, tab 18 is gripped and twisted, or otherwise manipulated with respect to anterior guard 10 to sever boss 20 from the end of cap 16 and form aperture 38, as illustrated in FIGS. 2 and 3. This aperture permits exteriorization of anterior needle 40 from within anterior guard 10 upon posterior axial translation of the anterior guard. Thereafter, sealing tape 14 is removed. Posterior guard 12 is translated posteriorly to expose hub 30 and the posterior needle enclosed within sheath 32, as shown in FIG. 2. The posterior end of the hub includes a posterior needle and sheath 32 insertable within a blood collection tube holder and a threaded section 34 which is engageable with the threads attendant the holder. In this manner, hub 30 is attached to the holder. (Since the attachment is well known, it is not shown for sake of clarity of illustration.)

Figures 4, 5, 7, 8A, 8B:
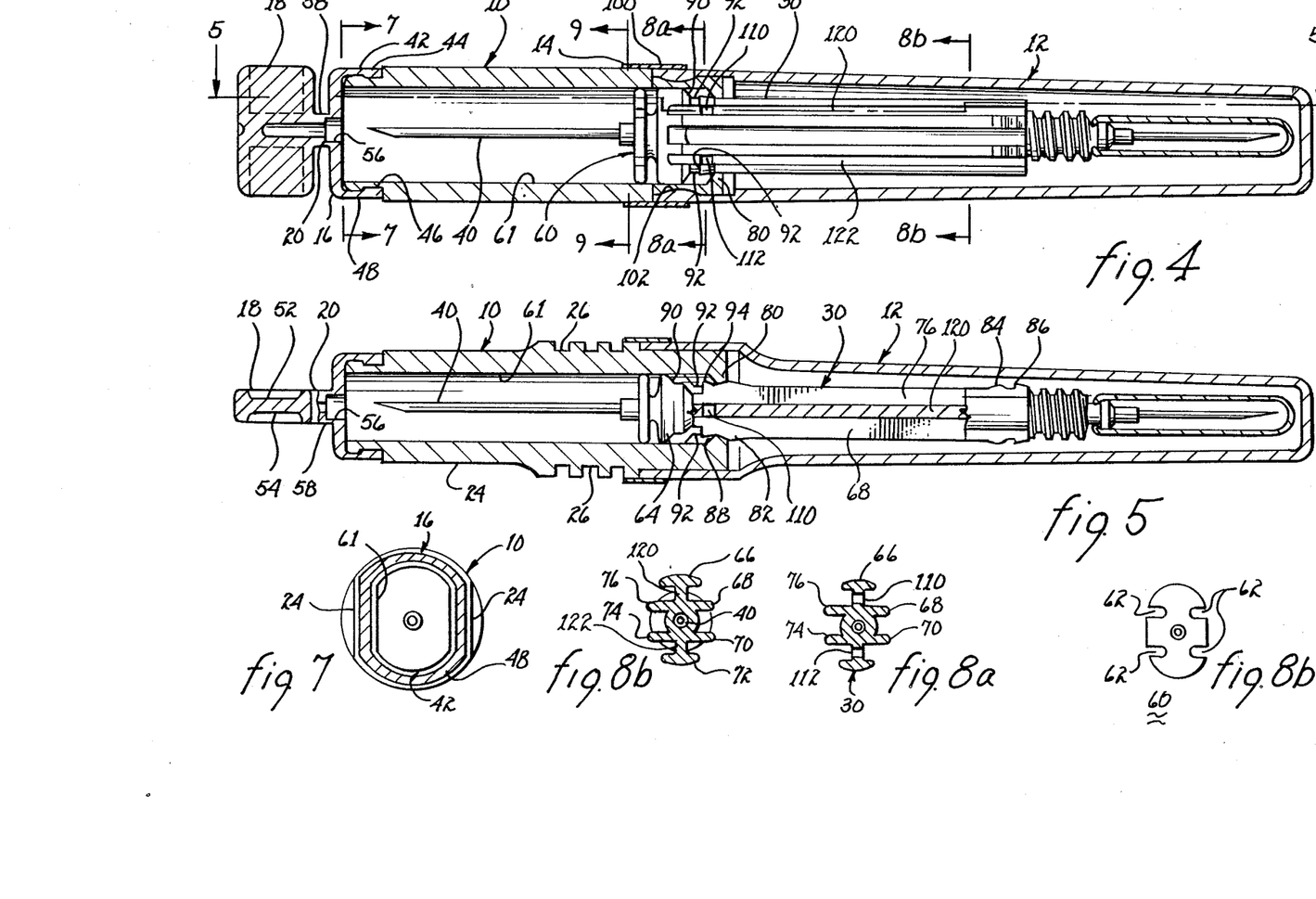
FIG. 4 is a side cross sectional view of the present invention.
FIG. 5 is a cross sectional view taken along lines 5—5, as shown in FIG. 4.
FIG. 7 is a cross sectional view taken along lines 7—7, as shown in FIG. 4.
FIG. 8a is a cross sectional view taken along lines 8a—8a, as shown in FIG. 4.
FIG. 8b is a cross sectional view taken along lines 8b—8b, as shown in FIG. 4.
Figure 10:
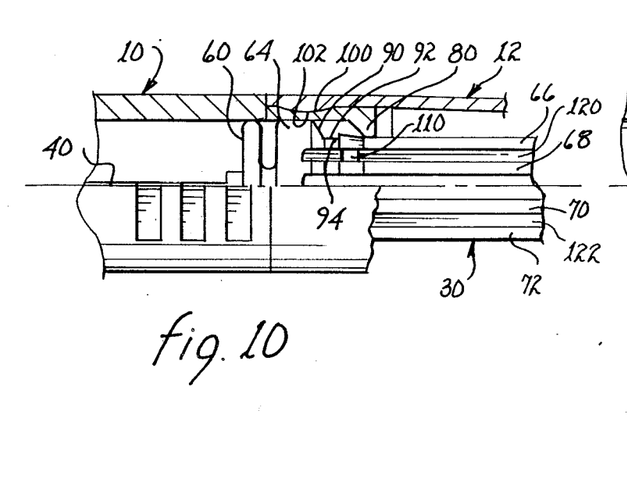
FIG. 10 is a partial cross sectional view showing the relationship at the junction between the anterior guard, the posterior guard and the hub prior to use.

FIGS. 4 and 5 illustrate certain details attendant cap 16. The anterior end of anterior guard 10 may include a ramp 42 defining, in part, an annular depression 44. A lip 46, extending inwardly from skirt 48 drops into and is retained within depression 44 upon attachment of the cap to secure the cap to the anterior guard. To assist in mounting of the cap upon the anterior guard, a ramp may be formed in conjunction with lip 46. The junction between cap 16 and anterior guard 10 may be a force fit to establish a seal therebetween; in addition, ultrasonic techniques or an adhesive may be employed to develop the point of attachment and seal. By employing a cap 16 to seal the anterior end of anterior guard 10, initial assembly of the anterior guard upon the double ended needle may be from the posterior end of the needle. Such assembly is preferred in that it permits construction of the anterior guard with a physical impediment to anteriorly oriented disengagement from the hub. To prevent inadvertent disengagement of the cap from the anterior guard, the cap may be formed to have a cross sectional area less than that of the adjacent part of the anterior guard. Thus, snagging of the cap at the junction is not likely to occur, which snagging might urge disengagement.

Referring jointly to FIGS. 4 through 10, certain details attendant the structural and operational relationships between anterior guard 10, posterior guard 12 and hub 30 will be described. Boss 20 in combination with cap 16 define a cavity 56 which produces a frangible skirt 58 of the boss. This skirt is ruptured upon application of a force to tab 18 relative to anterior guard 10; moreover, cavity 56, to the extent it is associated with cap 16, will define aperture 38 in order to ensure that such aperture is functionally dimensioned to permit exteriorizing anterior needle 40. Tab 18 may have formed therein opposed depressions 52, 54 to reduce the mass thereof for manufacturing purposes and to provide a more sure grip of the tab by user.

Hub 30 is generally oval in cross section in conformance with the cross sections of anterior guard 10 and posterior guard 12. It includes an anterior oval shaped flange 60. This flange serves a number of important functions. The interior dimension of anterior guard 10 preferably tapers posteriorly; this requires the initial assembly of the anterior guard to be from the posterior end of the hub. As the anterior guard is moved from the retracted to the extended position (moved anteriorly), the fit between flange 60 and interior surface 61 of the anterior guard becomes more and more tight. The tight fit between the flange and the anterior guard serves as support for the anterior guard to reduce any tendency of the anterior guard to wobble when in the extended position whether prior or subsequent to use of anterior needle 40. Furthermore, the flange will tend to guide the anterior guard during posterior translation to ensure exteriorization of the needle through aperture 38. To permit the flange to conform with the reduced taper of the anterior guard resulting in compression of the flange, a plurality of slots 62 may be formed therein, as illustrated in FIG. 9.

Hub 30 includes a piston 64 oval in cross section and conforming, generally, with the interior cross section of anterior guard 10. Because of the taper of the anterior guard, extension of the anterior guard will result in a tendency of the anterior guard to compress piston 64. Such compression establishes a tight fit therebetween and prevents the likelihood of separation between the hub and the anterior guard. Accordingly, piston 64 provides the function of a robust support for the anterior guard. The combination of support provided by flange 60 and piston 64 to the anterior guard helps assure against wobble of the anterior guard when the latter is in the extended position, against misalignment of the anterior needle with aperture 38, against disengagement between the anterior guard and the hub and against disruption of the locking apparatus when the anterior guard is in the third position.

Hub 30 includes a plurality of longitudinally oriented ridges 66, 68, 70, 72, 74 and 76, as particularly shown in FIG. 8b. These ridges are formed to reduce the mass of the hub and to facilitate certain manufacturing functions. Primarily, the ridges provide six axially oriented surface areas for supporting anterior guard 10 upon axial translation of the anterior guard with respect to hub 30. The posterior end of anterior guard 10 includes a radially inwardly extending ridge 80, which ridge, in cooperation with hub 30, supports the posterior end of the anterior guard. In the first position of anterior guard 10, the position prior to use, ridge 80 is located adjacent a ramp 82 extending radially from each of axial ridges 68, 70, 74, 76. These ramps discourage posterior translation of the anterior guard by interfering with ridge 80. However, the height of the ramps, in combination with the flexibility of the posterior end of the anterior guard, permits translation of the anterior guard posteriorly therepast upon application of a modest force to the anterior guard. Upon such translation, the anterior guard is retracted to expose anterior needle 40. The posterior end of hub 30 includes a ramp 84 extending radially outwardly from each of ridges 68, 70, 74, 76 and a lip 86 disposed upon each of the same axial ridges posteriorly displaced from ramps 84 by a space approximately equivalent to the width of annular ridge 80. Upon retraction of the anterior guard, ridge 80 is forced past ramps 84 into abutting relationship with lips 86. The effect of ramps 84 is that of discouraging annular ridge 80 from anterior movement therepast; they will cause anterior guard 10 to be selectively retained adjacent lips 86 in a second position corresponding to retraction of the anterior guard with anterior needle exposed ready for use.

Upon axial translation of the anterior guard from the second position, annular ridge 80 will accommodate translation past ramps 84 and ramps 82. Upon further anterior translation of anterior guard 10, side 88 of annular ridge 80 will abut sloping surface 90 of piston 64. Simultaneously, annular ridge 80 will become inwardly displaced within grooves 92 formed in each of axial ridges 66–76. Sides 94 of grooves 92 are generally radially oriented to discourage posteriorly oriented movement of annular ridge 80 therepast. As discussed above, anterior guard 10 tapers posteriorly. Accordingly, extension of the anterior guard anteriorly will produce an increasingly tighter fit between the anterior guard and each of flange 60 and piston 64. This tight fit, and the friction resulting therefrom, in combination with the mechanical impediment presented by side 94 of slots 92 against annular ridge 80 will serve the function of locking the anterior guard in the third or extended position. To assist a user in translating the anterior guard, diametrically opposed grooves 26, with the corresponding ridges formed thereby, provide a sure ripping surface. Furthermore, flats 24, which may be roughened, provide a further gripping surface for a user.

As illustrated in FIG. 4, posterior guard 12 may be secured to anterior guard 10 in an overlapping relationship. To assist in retaining the posterior guard secured in place, a shallow groove 100 may be formed in the posterior end of the anterior guard for receiving a similarly shallow radially inwardly oriented mound 102. The junction therebetween is covered or wrapped with tape 14.

Figure 11:
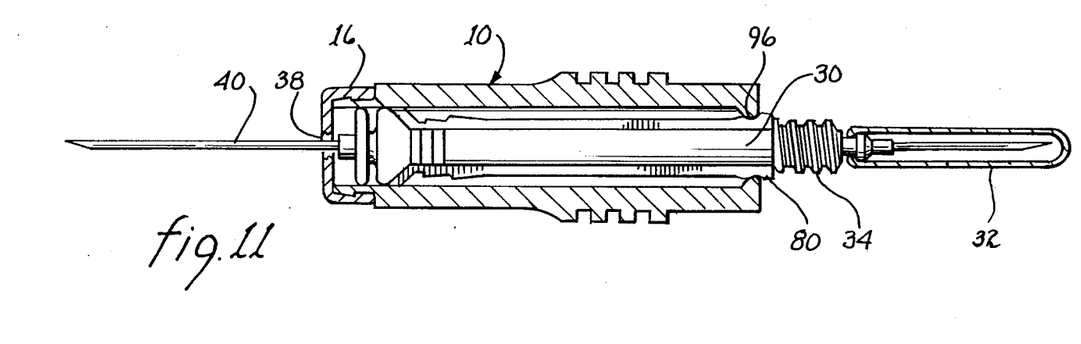
FIG. 11 is a partial cross sectional view showing the position of the anterior guard relative to the hub and ready for use.

Referring to FIG. 11, anterior guard 10 is shown in the second or retracted position with respect to hub 30. In this position, annular ridge 80 is disposed in slots 96 formed in ridges 68, 70, 74, 76. Anterior needle 40 has been exteriorized through aperture 38 of cap 16. Although a collection tube holder would normally be threadedly engaged with threaded section 34, it is not shown for purposes of clarity and illustration of the relationship between the anterior guard and the hub.

Figure 12:
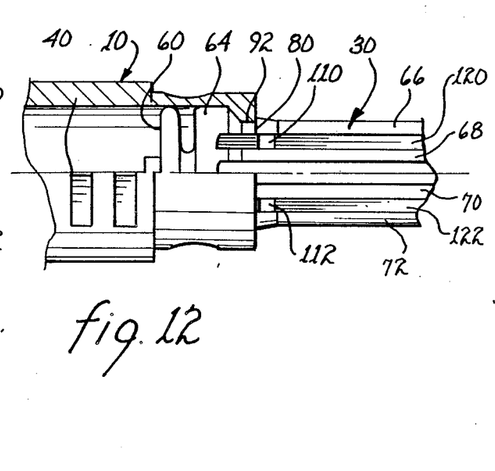
FIG. 12 is a partial cross sectional view showing the anterior guard in the locked position after use.

In FIG. 12, anterior guard 10 is shown in the third or extended position with respect to hub 30. In this position, the anterior needle is fully enclosed within the anterior guard, as shown in FIG. 6. In the extended or third position, annular ridge 80 is lockingly disposed in grooves 92 attendant hub 30, as described above. Both piston 64 and flange 60 have been slightly compressed due to the posterior tapering of the inner surface of the anterior guard. This compression, with the resulting tight fit between piston 64 and the interior surface of the anterior guard will stabilize the anterior guard with respect to the hub. It may also be noted that in the third or extended position of the anterior guard, it is stabilized by three annularly located and axially displaced points of support: flange 60, piston 64 and grooves 92. Such multipoint support will maintain the anterior guard stably located with regard to hub 30 and wobble thereof is essentially precluded and the likelihood of disengagement therebetween is substantially reduced.

The use of a hub having a plurality of axially aligned ridges for supporting the anterior guard results in several advantages. First, manufacturing considerations attendant shrinkage, cooling and accuracy of the part formed are enhanced. Second, unnecessary weight, without jeopardizing structural stability, is eliminated. Third, less material is used which will reduce manufacturing costs. Fourth, control of and support for translation of a guard therealong is more readily definable and controllable than that of a hub of solid mass. Thus, a hub having a plurality of longitudinal ridges represents an advance in the state of the art.

After use of the double ended needle for blood collection purposes, anterior guard 10 is axially translated anteriorly to the third position discussed above for the purpose of enclosing and sheathing needle 40 to prevent accidental needle stick. In the third position, ridge 80 extending radially inwardly and lodged within groove 92 of hub 30 is locked against posterior translation by side 94. Were ridge 80 not positioned within groove 92, posterior axial translation of anterior guard 10 might come about as a result of normal handling during the procedures attendant termination of the blood collection procedure and disposal of the double ended needle assembly. It is therefore of great importance to the safety of medical personnel that some positive indication be provided to confirm that the anterior guard is in the third position. Referring particularly to FIGS. 4, 5, 6, 8a and 12, structure for providing confirmation of the anterior guard being in the third position will be described.

At a point just posteriorly of anterior guard 10 when ridge 80 is disposed within grooves 92, hub 30 includes a pair of passageways 110, 112 extending therethrough. Such passageways, being exposed only upon locating anterior guard 10 in the third position, permit viewing of ambient light through the passageways. These two sources of light provide an unambiguous indication which is not dependent upon recognition of symbology upon a surface of the hub or similar non lighted type indicia. In practice, it has been found that even under low light conditions, the light radiating through passageways 110 and 112 is very visually apparent. As a result of the combination of ramps and grooves attendant hub 30 with which ridge 80 of the anterior guard cooperates, it is essentially impossible for the posterior end of the anterior guard to be in a position wherein passageways 110, 112 are not either fully uncovered or covered. That is, the anterior guard must be in its third position in order for any light to be visible through passageways 110, 112. Thus, the passageways provide an unambiguous visual indication of whether the anterior guard is or is not locked.

In the embodiment of hub 30 illustrated, passageway 110 is formed during manufacture of the hub by a pin or other means extending through the cavity wherein the hub is to be formed in transverse alignment with web 120. Passageway 112 is similarly formed by a pin or other means superimposed in a transverse alignment with web 122. The resulting passageways are particularly illustrated in FIG. 8a upon comparison with the cross section of the hub illustrated in FIG. 8b.

It may be noted that when anterior guard 10 is in the first position, ridge 80, as described above, is disposed posteriorly of a lateral plane wherein passageways 110, 112 lie. Accordingly, the posterior end of the anterior guard shields the passageways and they will not be visible to medical personnel using the present invention. Similarly, when the anterior guard is in the second position, the anterior part of the anterior guard will encircle and shield passageways 110, 112 from view.

In summary, passageways 110, 112 serving in the manner of a light source, provide an unambiguous indication that the anterior guard is in the third position and therefore locked in place to retain and enclose needle 40 therein. Because passageways 110, 112 function as a light source, they provide unambiguous visually perceivable indicia, even under low light ambient conditions, which conditions would be inadequate to positively recognize some other indicia that might be formed upon or associated with a surface of the hub.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirement without departing from those principles.

We claim:
1. A guard having a visually confirmable locked position for enclosing a needle extending from a hub to prevent uncovering of the needle and inadvertent needle stick after use of the needle, said guard comprising in combination:
   (a) means for locating said guard in a first position relative to the hub to maintain enclosed the needle within said guard prior to use of the needle;
   (b) means for posteriorly relocating said guard in a second position relative to the hub to exteriorize the needle from within said guard in preparation for use of the needle;
   (c) means for locking said guard in a third position upon anteriorly repositioning said guard relative to the hub to re-enclose the needle within said guard after use of the needle; and
   (d) means for providing a light transmissive passageway visually perceivable and unambiguously indicative of said guard being in the third position.

2. The guard as set forth in claim 1 wherein said guard includes radially inwardly extending means for supporting said guard upon the hub and means disposed in the hub for releasably capturing said supporting means when said guard is in each of the first and second positions.

3. The guard as set forth in claim 2 including means disposed in the hub for lockingly capturing said supporting means when said guard is in the third position.

4. The guard as set forth in claim 1 wherein said providing means is disposed in said hub.

5. The guard as set forth in claim 1 wherein said guard includes a posterior end for covering said passageway when said guard is located relative to the hub at any position other than in the third position.

6. The guard as set forth in claim 5 including a pair of passageways extending through the hub for accommodating transmission of light therethrough.

7. The guard as set forth in claim 1 wherein said guard includes a posterior end for covering said passageway when said guard is located relative to said hub at any position other than in the third position.

8. The guard as set forth in claim 7 including a pair of passageways extending through said hub for accommodating transmission of light therethrough.

9. The guard as set forth in claim 1 wherein said hub includes a plurality of longitudinally oriented ridges for guiding said guard along the hub upon relocating and repositioning said guard.

10. The guard as set forth in claim 9 wherein said locking means includes a radially inwardly extending ridge formed as part of said guard and a groove formed in at least some of said longitudinally oriented ridges for receiving said ridge of said guard.

11. The guard as set forth in claim 1 including two of said passageways, one of said passageways being located in each longitudinal half of the hub.

12. The guard as set forth in claim 11 wherein the hub includes a top longitudinal ridge, a bottom longitudinal ridge, a first pair of opposed longitudinal ridges connected to said top ridge by a first web and a second pair of opposed longitudinal ridges connected to said bottom ridge by a second web and wherein each of said passageways is disposed in one of said top and bottom webs.

13. The guard as set forth in claim 12 wherein the hub includes a longitudinal axis and wherein said pair of passageways are parallel with one another and transverse to the longitudinal axis of the hub.

14. The guard as set forth in claim 1 wherein said guard includes a cap disposed at the anterior end of said guard for enclosing the anterior end of said guard prior to use of the needle, said cap including a frangibly attached tab for developing an aperture in said cap through which the needle may be exteriorized.

15. The guard as set forth in claim 14 wherein said tab includes a frangible boss for developing the aperture.

16. The guard as set forth in claim 14 wherein said cap is of lesser cross section than said anterior guard to minimize a likelihood of snagging said cap.

17. The guard as set forth in claim 1 wherein the needle is a double ended needle having an anterior needle and a posterior needle extending from opposed ends of the hub, said anterior guard being associated with the anterior needle and including a posterior guard for enclosing the posterior needle before and after use of the double ended needle.

18. The guard as set forth in claim 17 including means for releasably attaching said posterior guard to said anterior guard in overlapping relationship.

19. The guard as set forth in claim 18 including means for sealing the junction between said anterior guard and said posterior guard.

20. A guard having a visually confirmable locked position for enclosing a needle extending from a hub to prevent uncovering of the needle and inadvertent needle stick after use of the needle, said guard comprising in combination:
   (a) means for locating said guard in a first position relative to the hub to maintain enclosed the needle within said guard prior to use of the needle;
   (b) means for posteriorly relocating said guard in a second position relative to the hub to exteriorize the needle from within said guard in preparation for use of the needle;
   (c) radially inwardly extending means for supporting said guard upon the hub and means disposed in said hub for releasably capturing said supporting means when said guard is in each of the first and second positions;
   (d) means for locking said guard in a third position upon anteriorly repositioning said guard relative to the hub to re-enclose the needle within said guard after use of the needle, said locking means including means disposed in said hub for lockingly capturing said supporting means when said guard is in the third position; and
   (e) means for providing at a location posterior of said guard a visually perceivable unambiguous indication of said guard being in the third position, said providing means including at least one passageway extending through said hub for transmitting light therethrough.

21. A guard having a visually confirmable locked position for enclosing a needle extending from a hub to prevent uncovering of the needle and inadvertent needle stick after use of the needle, said guard comprising in combination:
   (a) means for locating said guard in a first position relative to the hub to maintain enclosed the needle within said guard prior to use of the needle;
   (b) means for posteriorly relocating said guard in a second position relative to the hub to exteriorize the needle from within said guard in preparation for use of the needle;
   (c) means for locking said guard in a third position upon anteriorly repositioning said guard relative to the hub to re-enclose the needle within said guard after use of the needle; and
   (d) means for providing at a location posterior of said guard a visually perceivable unambiguous indication of said guard being in the third position, said providing means including at least one passageway extending through said hub for accommodating transmission of light therethrough.

22. A guard having a visually confirmable locked position for enclosing a needle extending from a hub to prevent uncovering of the needle and inadvertent needle stick after use of the needle, said guard comprising in combination:
   (a) means for locating said guard in a first position relative to the hub to maintain enclosed the needle within said guard prior to use of the needle;
   (b) means for posteriorly relocating said guard in a second position relative to the hub to exteriorize the needle from within said guard in preparation for use of the needle;
   (c) means for locking said guard in a third position upon anteriorly repositioning said guard relative to the hub to re-enclose the needle within said guard after use of the needle, said locking means including a radially inwardly extending ridge formed as part of said guard and a groove formed in at least some of said longitudinally oriented ridges for receiving said ridge of said guard;
   (d) a plurality of longitudinally oriented ridges for guiding said guard along the hub upon relocating and repositioning said guard; and
   (e) means for providing at a location posterior of said guard a visually perceivable unambiguous indication of said guard being in the third position, said providing means including at least one light transmissive passageway extending through the hub posteriorly of any of said grooves.

23. A method for providing a visual indication to confirm locked enclosure within a guard of a needle extending from a hub to prevent uncovering of the needle and inadvertent needle stick after use of the needle, the guard being located relative to the hub in a first position to enclose the needle within the guard prior to use of the needle, said method comprising the steps of:
   (a) relocating the guard posteriorly to a second position relative to the hub to exteriorize the needle from the guard in preparation for use of the needle;
   (b) locking the guard in a third position upon anterior repositioning of the guard relative to the hub to reenclose the needle within the guard after use of the needle, and;
   (c) providing a light transmissive passageway visually perceivable and unambiguously indicative of the guard being in the third position.

24. The method as set forth in claim 23 wherein the hub supports a double ended needle extending anteriorly and posteriorly of the hub and wherein said steps of relocating and locking are associated with the guard for the anterior needle, said method including the step of attaching a posterior guard relative to the hub to enclose the posterior needle.

25. The method as set forth in claim 24 wherein said step of attaching includes the step of securing sealing tape about the junction of the anterior guard and the posterior guard.

26. A method for providing a visual indication to confirm locked enclosure within a guard of a needle extending from a hub to prevent uncovering of the needle and inadvertent needle stick after use of the needle, the guard being located relative to the hub in a first position to enclose the needle within the guard prior to use of the needle, said method comprising the steps of:
   (a) relocating the guard posteriorly to a second position relative to the hub to exteriorize the needle from the guard in preparation for use of the needle;
   (b) locking the guard in a third position upon anterior repositioning of the guard relative to the hub to reenclose the needle within the guard after use of the needle, and;
   (c) providing at a location posterior of the guard a visually perceivable unambiguous indication of the guard being in the third position, said step of providing including the step of accommodating visually perceivable transmission of light through a transversely oriented passageway disposed in the hub and only when the guard is in the third position.

27. A method for providing a visual indication to confirm locked enclosure within a guard of a needle extending from a hub to prevent uncovering of the needle and inadvertent needle stick after use of the needle, the guard being located relative to the hub in a first position to enclosure the needle within the guard prior to use of the needle, said method comprising the steps of:
  (a) relocating the guard posterior to a second position relative to the hub to exteriorize the needle from the guard in preparation for use of the needle;
  (b) locking the guard in a third position upon anterior repositioning of the guard relative to the hub to reenclose the needle within the guard after use of the needle, and;
  (c) providing at a location posterior of the guard a visually perceivable unambiguous indication of the guard being in the third position; and
  (d) a pair of transversely oriented passageways disposed in the hub for transmitting light and including the step of shielding the pair of passageways in the hub with the guard to prevent visually perceivable transmission of light through the pair of passageways whenever the guard is in other than the third position.

28. A guard having a visually confirmable locked position for enclosing a needle extending from a needle supporting element to prevent uncovering of the needle and inadvertent needle stick after use of the needle, said guard comprising in combination:
  (a) means for locating said guard in a position of use relative to the needle supporting element and with the needle exteriorized of said guard in preparation for use of the needle;
  (b) means for locking said guard in a locked position upon anteriorly repositioning said guard relative to the needle supporting element to enclose the needle within said guard after use of the needle; and
  (c) light transmissive means for providing a visually perceivable unambiguous indication of said guard being in the locked position.

29. The guard as set forth in claim 28 wherein said guard includes radially inwardly extending means for supporting said guard upon the needle supporting element and means disposed in the needle supporting element for releasably capturing said supporting means when said guard is in the position of use.

30. The guard as set forth in claim 29 including means disposed in the needle supporting element for lockingly capturing said supporting means when said guard is in the locked position.

31. The guard as set forth in claim 28 wherein said light transmissive means includes at least one passageway extending through the needle supporting element for transmitting light through the needle supporting element.

32. The guard as set forth in claim 31 wherein said guard includes a posterior end for covering said passageway when said guard is located relative to the needle supporting element at any position other than in the locked position.

33. The guard as set forth in claim 31 including a pair of passageways extending through the needle supporting element for accommodating transmission of light therethrough.

34. The guard as set forth in claim 1 wherein the needle supporting element includes a plurality of longitudinally oriented ridges for guiding said guard along the needle supporting element upon repositioning said guard.

35. The guard as set forth in claim 34 wherein said locking means includes a radially inwardly extending ridge formed as part of said guard and a groove formed in at least some of said longitudinally oriented ridges for receiving said ridge of said guard.

36. The guard as set forth in claim 35 wherein said light transmissive means includes at least one light transmissive passageway extending through the needle supporting element posteriorly of any of said grooves.

37. The guard as set forth in claim 36 including two of said passageways, one of said passageways being located in each lateral half of the needle supporting element.

38. The guard as set forth in claim 37 wherein the needle supporting element includes a top longitudinal ridge, a bottom longitudinal ridge, a first pair of opposed longitudinal ridges connected to said top ridge by a first web and a second pair of opposed longitudinal ridges connected to said bottom ridge by a second web and wherein each of said passageways is disposed in one of said top and bottom webs.

39. The guard as set forth in claim 28 wherein said guard includes a cap disposed at the anterior and of said guard for enclosing the anterior end of said guard prior to use of the needle, said cap including a frangibly attached tab for developing an aperture in said cap through which the needle may be exteriorized.

40. The guard as set forth in claim 28 wherein the needle is a double ended needle having an anterior needle and a posterior needle extending from opposed ends of the needle supporting element, said guard comprising an anterior guard associated with the anterior needle and including a posterior guard for enclosing the posterior needle before and after use of the double ended needle.

41. The guard as set forth in claim 40 including means for releasably attaching said posterior guard to said anterior guard in overlapping relationship.

42. The guard as set forth in claim 41 including means for sealing the junction between said anterior guard and said posterior guard.

43. A method for providing a visual indication to confirm locked enclosure within a guard of a needle extending from a needle supporting means to prevent uncovering of the needle and inadvertent needle stick after use of the needle, said method comprising the steps of:
  (a) locating the guard in a position of use relative to the needle supporting element with the needle exteriorized from the guard in preparation for use of the needle;
  (b) locking the guard in a locked position upon anterior repositioning of the guard relative to the needle supporting element to enclosure the needle within the guard after use of the needle; and
  (c) providing a visually perceivable unambiguous light transmissive indication of the guard being in the locked position.

44. The method as set forth in claim 43 wherein the needle supporting element supports a double ended needle extending anteriorly and posteriorly of the needle supporting element and wherein said steps of locating and locking are associated with the guard for the anterior needle, said method including the step of attaching a posterior guard relative to the needle supporting element to enclose the posterior needle.

45. The guard as set forth in claim 44 wherein the needle supporting element includes at least one transversely oriented light transmissive passageway, said step of providing including the step of accommodating visually perceivable transmission of light through the passageway in the needle supporting element only when the guard is in the locked position.

46. The guard as set forth in claim 44 wherein the needle supporting element includes a pair of transversely oriented light transmissive passageways and including the step of shielding the pair of passageways in the needle supporting element with the guard to prevent visually perceivable transmission of light through the pair of passageways whenever the guard is in other than the locked position.

* * * * *